US007087430B2

(12) United States Patent
Herman et al.

(10) Patent No.: US 7,087,430 B2
(45) Date of Patent: Aug. 8, 2006

(54) HUMAN VNO CDNA LIBRARIES

(75) Inventors: Ronald C. Herman, Sunnyvale, CA (US); David L. Berliner, Atherton, CA (US)

(73) Assignee: Pherin Pharmaceuticals, Inc., Redwood City, CA (US)

( * ) Notice: Subject to any disclaimer, the term of this patent is extended or adjusted under 35 U.S.C. 154(b) by 282 days.

(21) Appl. No.: 10/461,803

(22) Filed: Jun. 12, 2003

(65) Prior Publication Data

US 2003/0224440 A1  Dec. 4, 2003

Related U.S. Application Data

(63) Continuation of application No. 09/783,252, filed on Feb. 13, 2001, now abandoned.

(60) Provisional application No. 60/183,128, filed on Feb. 17, 2000.

(51) Int. Cl.
*C12N 5/06* (2006.01)
(52) U.S. Cl. .................................... 435/326; 536/23.1
(58) Field of Classification Search .................. 435/6; 536/23.1
See application file for complete search history.

(56) References Cited

U.S. PATENT DOCUMENTS

| 5,858,731 A | 1/1999 | Sorge et al. ............... 435/91.1 |
| 5,891,636 A | 4/1999 | Van Gelder .................... 435/6 |
| 5,994,623 A | 11/1999 | Broglie et al. .............. 800/278 |

FOREIGN PATENT DOCUMENTS

| WO | WO 97/14790 | 4/1997 |
| WO | WO 99/00422 | 1/1999 |
| WO | WO 9900422 A1 * | 1/1999 |
| WO | WO 01/25431 | 4/2001 |

OTHER PUBLICATIONS

Axel, "The Molecular Logic of Smell", Scientific American, Oct. 1995, pp. 154-159.
Barinaga, "Salmon Follow Watery Odors Home", Science, Oct. 22, 1999, vol. 286, pp. 705-706.
Berliner, D. L. 1996. J. Steroid Biochem Molec Biol 58:1-2.
Berliner, D. L., L. Monti-Bloch, C. Jennings-White and V. Diaz-Sanchez 1996. J Steroid Biochem, Molec Biol 58:259-265.
Broadwell, R. D. 1975. J Comp Neurol 163:329-346.
Cao, Y., B. C. Oh, and L. Stryer. 1998. Proc Natl Acad Sci USA 95:11987-11992.
Dulac, et al, "A novel family of genes encoding putative pheromone receptors in mammals", Cell, Oct. 20, 1995, 83; (2); pp. 195-206, XP002156990, United States.
Gaafar, H, A, A. A. Tantawy, A. A. Melis, D. M. Hennawy and H. M. Shehata, 1998, Acta Otolargyngol 118:408-412.

Gruber, et al., "Construction of SuperScript Human cDNA Libraries", Focus 17 No. 2, pp. 43-44.
Herrada, et al., "A novel family of putative pheromone receptors in mammals with a topographically organized and sexually dimorphic distribution", Cell, Aug. 22, 1997, 90; (4); pp. 763-773, XP002913897, United States.
Jacob, "Human Pheromones", The Physiology of Taste, http://www.cf.ac.uk/uwcc/momed/jacob/teaching/sensory/pherom.html.
Kallmann, F., W. A. Schoenfeld and S. E. Barrera. 1943. Am J Ment Defic 48:203-236.
Kel, A., A. Ptitsyn V. Babenko, S. Meier-Ewert, and H. Lebrach. 1998. Bioinformatics 14:259-270.
Keverne, et al, "The vomeronasal organ", Science, American Association For The Advancement of Science, U.S., vol. 286, No. 5440, Oct. 22, 1999, pp. 716-720, XP002157783, ISSN: 0036-8075.
Kevetter et al, "Connection of the Corticomedial Amygdala in the Golden Hamster. I. Efferents of the Vomeronasal Amygdala", J of Comparative Neurology 197:81-89 (1991).
Krieger, et al., "Olfactory Reception in Invertebrates", Science, Oct. 22, 1999, vol. 286, pp. 720-723.
Krieger, J., A. Schmitt, D. Löbel, T. Gudermann, G. Schultz, H. Breer, and I. Boekhoff. 1999. J Biol Chem 274:4656-4662.
Laurent, "A Systems Perspective On Early Olfactory Coding", Science, Oct. 22, 1999, vol. 286, pp. 723-728.
Luscher, M. and P. Karlson. 1959. Nature 18:55-56.
Malakoff, "Following The Scent of Avian Olfaction", Science, Oct. 22, 1999, vol. 286, pp. 704-705.
Matsunami, H. and L. B. Buck, 1997, Cell 90:775-784.
Meredith, M., 1983, in Pheromones and reproduction in mammals (Vandenbergh, ed.) pp. 199-252, Academic Press.
Mombaerts, "Seven-Transmembrane Proteins as Odorant and Chemosensory Receptors", Science, Oct. 22, 1999, vol. 286, pp. 707-711.

(Continued)

*Primary Examiner*—Gary Benzion
*Assistant Examiner*—Christopher M Babic
(74) *Attorney, Agent, or Firm*—Heller Ehrman LLP; James A. Fox

(57) ABSTRACT

This invention relates to DNA libraries, in particular a human VNO cDNA library is described. Pheromone receptor cDNA once isolated is transfected into competent cells. The transfected cell lines provide a scaleable source of homogeneous material to develop efficient, automated high throughput screening assays for new vomeropherins, and thereby reduce the ongoing need for human volunteers in the preclinical phases of drug discovery. Identification and characterization of the human VNO receptor(s) will facilitate the development and commercialization of vomeropherins with improved specificity, and enhanced therapeutic efficacy in the treatment of the target diseases.

4 Claims, 1 Drawing Sheet

OTHER PUBLICATIONS

Monti-Bloch, L. 1997. Chemical Senses 22:752.
Monti-Bloch, L. and B. I. Grosser. 1991. J. Steroid Biochem. Molec. Biol. 39:573-582.
Monti-Bloch, L. V. Diaz-Sanchez, C. Jennings-White and D. L. Berliner. 1998a. J. Steroid Biochem. Molec. Biol. 65:237-242.
Monti-Bloch, L, C. Jennings-White and D. L. Berliner. 1998b. Ann. N.Y. Acad. Sci. 855:373-389.
Monti-Bloch, L., C. Jennings-White, D. S. Dolberg and D. L. Berliner, 1994, Pyschoneuroendocrinology 19:673-686.
Moran, D. T., B. W. Jafek and J. C. Rowley III. 1991, J Steroid Biochem Molec Biol 39:545-552.
Mori, et al., "The Olfactory Bulb: Coding and Processing Of Odor Molecule Information", Science, Oct. 22, 1999, vol. 286, pp. 711-715.
Quinton, Gonadotropin-Releasing Hormone Immunoreactivity in the Nasal Epithelia of Adults with Kallmann's Syndrome and Isolated Hypogonadotropic Hypogonadism and in the Early Midtrimester Human Fetus, The Journal of Clinical Endocrinology & Metabolism, Jan. 1997, vol. 82, No. 1, pp. 309-314, ISSN: 0021-972X.
Rodriguez, et al., "A putative pheromone receptor gene expressed in human olfactory mucosa", Nature Genetics, Nature America, New York, U.S., vol. 26, Sep. 2000, pp. 18-19, XP002157781, ISSN: 1061-4036.
Ryba, N. J. P. and R. Tirindelli. 1997. Neuron 19:371-379.
Saito, H., M. L. Mimmack, E. B. Keverne, J. Kishimoto and P. C. Emson. 1998. Brain Res Molec Brain Res 60:215-227.
Schaeren-Wiemers, N. and A. Gerfin-Moser. 1993. Histochemistry 100:431-440.
Simon, M. I., M. P. Strathmann, and N. Gautam, 1991, Science 252:802-808.
Simms, et al., "TRIzol: A New Reagent for Optimal Single-Step Isolation of RNA", Focus 15, No. 4, pp. 99-102.
Smith, T. D., M. I. Siegel, A. M. Burrows, M. P. Mooney, A. R. Burdi, P. A. Fabrizio and F. R. Clemente, 1998, Micro Res Tech 41:483-491.
Sobel, N., V. Prabhakaran, C. A. Hartley, J. E. Desmond, G. H. Glover, E. V. Sullivan and J. D. E. Gabrieli. 1999, Brain 122:209-217.
Stern et al., "Making Sense of Scents", Science vol. 286, Oct. 22, 1999, pp. 703.
Stern, K. and M. K. McClintock. 1998, Nature 392:177-179.
Takami, S., M. L. Getchell, Y. Chen, L. Monti-Bloch, D. L. Berliner, L. J. Stenaas, and T. V. Getchell. 1993, Neuroreport 4:375-378.
Velasco, G., et al, "Nose Surgery and the Vomeronasal Organ", Aesthetic Plastic Surgery 19:451-454, 1995.
Wysocki, C. J. 1979. Neurosci Biobehav Rev 3:301-341.
Wysocki, C. J. and J. J. Lepri. 1991. J. Steroid Biochem Molec Biol 39:661-669.

* cited by examiner

HUMAN VNO CDNA LIBRARIES

RELATED APPLICATIONS

This application is a continuation of application Ser. No. 09/783,252, filed Feb. 13, 2001, which claims the priority under 35 USC 119(e) of Provisional Application No. 60/183,128, filed Feb. 17, 2000.

FIELD OF THE INVENTION

The present invention relates generally to the field of cDNA libraries, and more specifically to human vomeronasal organ libraries.

BACKGROUND

Small, volatile and non-volatile organic molecules, commonly referred to as pheromones, mediate species-specific chemical communication between terrestrial animals. Pheromones are present in the secretions and excretions from various organs and tissues, including the skin, and represent diverse families of chemical structures. Pheromones play essential roles in sexual activity, reproductive biology, and other innate animal behaviors (Luscher et al., (1959) Nature 18:55–56; Meredith (1983) in Pheromones and Reproduction in Mammals (Vandenbergh, ed.) pp. 199–252, Academic Press; Stern et al., (1998) Nature 392: 177–179; Wysocki, (1979) Neurosci. Biobehav. Rev. 3:301–341; Jacob et al., (2000) Hormones and Behavior 37:57–78; Grosser et al., (2000) Psychoneuroendocrinology 25:289–299). Some, but not all, terrestrial vertebrates detect pheromones in the vomeronasal organ (the VNO), also known as Jacobson's organ, a small dead-end tubular structure with an opening into the nasal cavity that is located bilaterally at the base of the nasal septum (Moran et al., (1991) J. Steroid Biochem. Molec. Biol. 39:545–552.).

The VNO was first identified in humans in 1703 but it was believed to be a vestigial organ without function in the adult. In the 1990s, the presence of a VNO was established, caudal to the nasal septal cartilage on both sides of the nasal septum, in more than 1700 normal male and female human subjects (Berliner, (1996) J. Steroid Biochem. Molec. Biol. 58:1–2; Gaafar et al., (1998) Acta Otolargyngol. 118:408–412; Smith et al., (1998) Micro. Res. Tech. 41:483–491) The VNO is physically separate and functionally distinct from the olfactory epithelium that detects the volatile odorants. Odorants do not bind to the VNO receptors.

The VNO is lined with neuroepithelial cells with a microvillar surface that is the presumptive site of pheromone receptors. Immunohistochemical staining of adult human VNO epithelium detects neuron-specific enolase and protein gene product (PGP) 9.5, both neuronal and neuroendocrine markers, in some bipolar cells with morphological similarities to olfactory receptor neurons (Takami et al., (1993) Neuroreport 4:375–378). More recent studies show that the majority of the cells lining the lumen of the human VNO stain with antibodies to synaptophysin or chromogranin which are also markers for neuronal and neuroendocrine cells. These data provide clear evidence for the existence of a neuroepithelium in the human VNO. However, Takami et al. (1993) do not detect olfactory marker protein (OMP) in the human VNO even though it is expressed in the VNO of other vertebrates including rodents. This may reflect an important and interesting species difference between humans and other vertebrates.

In animals, signals from the olfactory epithelium travel via the olfactory bulb to the olfactory cortex and then on to other regions of the brain. In contrast, signals from the VNO are transmitted through the accessory olfactory bulb to the amygdala and hypothalamus (Broadwell et al., (1975) J. Comp. Neurol. 163:329–346; Kevetter et al., (1981) J. Comp. Neurol. 197:81–98). Surgical ablation of the VNO in male rodents alters a variety of endocrine-mediated responses to female pheromones including androgen surges, vocalization, territorial marking, and inter-male aggression. Ablation of the VNO in female rodents delays or prevents activation of reproduction, abolishes the effects of overcrowding on sexual maturation, and reduces maternal responses to intruders (Wysocki et al., (1991) J. Steroid Biochem. Molec. Biol. 39:661–669). In humans, the defect (s) that causes the inherited hypogonadal disorder, Kallmann Syndrome, is also associated with defective development of the VNO-terminalis complex (Kallmann et al., (1943) Am. J. Ment. Defic. 48:203–236).

Application of only femtomole quantities of any of several proprietary, synthetic vomeropherins directly to the VNO of human volunteers rapidly induces reproducible negative voltage potentials that can be measured locally with a multifunctional miniprobe. The electrophysiological response in the VNO is characteristic of a mass receptor potential. The magnitude of the response is dose-dependent and is accompanied by changes in autonomic nervous system function, brain wave activity, gonadotropin secretion, and mood (Berliner et al., (1996) J Steroid Biochem, Molec. Biol. 58:259–265; Monti-Bloch et al. (1998a) J. Steroid Biochem. Molec. Biol. 65:237–242; Monti-Bloch et al., (1998b) Ann. N.Y. Acad. Sci. 855:373–389; Monti-Bloch et al., (1994) Pyschoneuroendocrinology 19:673–686; Monti-Bloch et al., (1991) J. Steroid Biochem. Molec. Biol. 39:573–582; Grosser et al., (2000) Psychoneuroendocrinology 25:289–299).

Recent FMRI studies detect dose-dependent activation of the anterior medial thalamus, the inferior frontal gyrus, and other regions of the human brain, in the absence of detectable odor, following administration of estra-1,3,5(10),16-tetraen-3yl acetate (PH15) to human volunteers. Although Sobel et al. ((1999) Brain 122:209–217) deliver the compound non-specifically to the nasal cavity in these fMRI tests, Monti-Bloch et al. (1994) have demonstrated that this compound induces physiological responses in vivo only when applied specifically to the VNO but not when applied to either olfactory or respiratory epithelium of human subjects. Therefore, the fMRI data support the existence of a functional neurological connection between the VNO and the human brain which can be activated by a vomeropherin.

Administration of naturally occurring compounds of known structure such as estra-1,3,5(10),16-tetraen-3-ol and androsta-4,16-dien-3-one to the human VNO induce bradycardia, bradypnea, increases in core body temperature, and other physiological responses. Stern et al. (1998) have demonstrated that odorless human pheromones, obtained from the axillae of women at different stages of the menstrual cycle, exert opposing effects on ovulation when applied above the lips where they can volatilize into the nasal cavity of recipient females. Some vomeropherins act exclusively in human females or in males, and others exert opposite effects on autonomic reflexes such as body temperature. Taken together, these data provide substantial support for the existence of a functional VNO in humans with the capacity to exert significant physiological effects in vivo.

The VNO system affords the unique opportunity to develop and market novel therapeutics to treat disease via previously unexploited targets and neurological pathways. This approach has substantial benefits for the patient over existing therapies including: (i) the ease of delivery to the VNO, (ii) the requirement for only picograms of drug, (iii) the rapid response to drug, and (iv) the apparent absence of the side-effects and toxicity frequently associated with systemic (e.g., oral) delivery of drug. Thus, targeting receptors in the human VNO for the treatment of disease is desirable.

The standard bioassay for screening candidate vomeropherins requires the participation of human volunteers because pheromones are species-specific. In this assay, the compounds are delivered directly to the VNO of volunteers under IRB-approved protocols, thus necessitating prior toxicological study of each candidate vomeropherin in rodents. This expensive and time-consuming process limits the number of compounds that can be tested and hampers the detailed structure-activity relationship (SAR) analyses that are essential to successful drug discovery.

Viable neuroepithelial cells may be harvested directly from the human VNO for testing in vitro. The harvested VNO cells retain their characteristic neuroepithelial morphology in culture and respond electrophysiologically to the application of vomeropherins in vitro, thereby demonstrating the existence of functional receptors in cells from the target tissue. Although this method still requires the participation of human volunteers, it increases the screening throughput and decreases the number of animals required for toxicological studies. However, only a limited number of non-dividing cells with a ~2-week life-span are obtained from each volunteer, and thus we require an entirely new approach to meet the demands of modem high throughput drug screening and SAR.

Several groups have cloned receptor cDNAs that are expressed exclusively in the VNO of rats and mice, but, to date, no one has cloned human VNO receptor cDNAs. The sequence of the cloned rodent receptor cDNAs indicates that they belong to the superfamily of G protein-coupled receptors containing seven transmembrane domains, but they are unrelated to any of the G protein-coupled receptors expressed in the olfactory epithelium (Dulac et al, (1995) Cell 83:495–206; Herrada et al., (1997) Cell 90:763–773; Matsunami et al., (1997) Cell 90:775–784; Ryba et al., (1997) Neuron 19:371–379; Saito et al., (1998) Brain Res. Molec. Brain Res. 60:215–227). Database comparisons identify motifs common to $Ca^{2+}$-sensing and metabotropic glutamate receptors in some of the clones. The apparent lack of homology to olfactory receptors is consistent with the observation that many vomeropherins are inactive when applied specifically to human olfactory epithelium in vivo.

Each cloned rodent receptor messenger RNA (mRNA) is detected by in situ hybridization in only a small number of neuroepithelial cells that are dispersed throughout the rodent VNO, and it is likely that each cell expresses only a single receptor gene. (Dulac et al., 1995; Herrada et al., 1997; Matsunami et al., 1997; Ryba et al., 1997; Saito et al., 1998). Some of the cloned rodent receptors exhibit sexually dimorphic expression, i.e., they are expressed differently in males or females.

The rodent VNO receptors are assigned to separate multigene families by two criteria: (i) the length of the extracellular (N-terminal) protein domain, and (ii) the isoform of the signal-transducing G protein co-expressed in the same cell. Receptors in the "V1R" family have a relatively short extracellular N-terminal domain and are expressed primarily in cells that express a $G\alpha_t$ isoform of G protein. Receptors in the "V2R" family have a long extracellular N-terminal domain and are expressed primarily in cells that express a $G\alpha_0$ isoform of G protein. Differences at the N-terminus between the V1R and V2R families may reflect differences in the structure of the ligand and/or in the location of the ligand-binding domain. (Matsunami et al., 1997; Ryba et al., 1997; Krieger et al., (1999 J. Biol. Chem. 274:4656–4662). Neuroepithelial cells expressing these distinct G protein isoforms are spatially segregated in the VNO in separate apical and basal longitudinal zones, suggesting that there is true physiological significance to the differences between the V1R and V2R receptor families.

Krieger et al. (1999) have recently shown that G protein-coupled receptors expressed in the rodent VNO are functionally linked to signal transduction pathways. Their results demonstrate that volatile and non-volatile pheromonal components of male rat urine selectively activate the major Gα protein subtypes ($G_i$ and $G_0$, respectively) expressed in the VNO of female rats. The data imply that V1R family receptors, which are co-expressed with $G_i$, respond to volatile compounds whereas V2R family receptors, which are co-expressed with $G_0$, respond to non-volatile protein components of urine.

Dulac and Axel (1995) estimate that, in total, the rat V1R family contains approximately 35 candidate pheromone receptors; Herrada and Dulac (1997) and Ryba and Tirindelli (1997) estimate that the rat V2R family contains an additional 100 receptors. Of the various rodent tissues tested, only mRNA from the VNO gives a positive signal on northern blots probed with the cloned ($^{32}$P-labeled) pheromone receptor cDNAs. At this limit of sensitivity, these results suggest that the pheromone receptors are expressed exclusively (primarily) in the VNO. At the present time, it is not known if each VNO receptor recognizes a distinct pheromone or if several receptors recognize the same compound.

At reduced stringency, the cloned rodent VNO receptor cDNAs cross-hybridize to human genomic DNA. Dulac and Axel (1995) detect approximately 15 human genes that cross-hybridize to rat V1R family probes, and Herrada and Dulac (1997) detect an additional ten human homologues that cross-hybridize to rat V2R family probes. The two sequenced human V1R genomic DNA clones have ~40–50% identity with the closest rat homologue. However, both human genomic clones have a stop codon in the putative coding region and may thus be pseudogenes (Dulac and Axel, 1995). Nevertheless, cross-hybridization suggests the evolutionary conservation of G protein-coupled receptors in the VNO and thereby provides a means to isolate human receptor clones.

The presence of these pseudogenes does not preclude the existence of functional human VNb receptor genes, especially in view of our assays with cells harvested directly from the VNO (Monti-Bloch (1997) Chemical Senses 22:752). The past difficulties in isolating, characterizing and cloning a VNO receptor reinforce our assertion that an appropriate way to isolate functional clones of the human VNO receptors is via cDNA prepared directly from the target tissue. In fact, Cao et al. ((1998) Proc. Nad. Acad. Sci. USA 95:11987–11992) have successfully isolated homologues from a goldfish cDNA library using probes based on the rodent receptor sequences even though that species lacks a defined VNO. The presence of pseudogenes in the family has not prevented the successful cloning of olfactory or VNO receptors from a variety of species and they should present no greater obstacle to the cloning of human VNO receptors.

Thus, isolation and characterization of the human VNO receptors is desirable for the development of new drugs, high throughput assays and characterization of the receptors and their signal transduction pathways.

SUMMARY

In one aspect of the invention there is a cDNA library prepared from the normal human female VNO.

In a second aspect of the invention there is provided human VNO receptor cDNA sequences.

In a further aspect there is provided transformed cells expressing a functional human VNO receptor.

In another aspect of the invention there is provided a human VNO cell culture expressing a functional pheromone receptor.

In yet another aspect there is provided a high throughput drug screening assay.

DESCRIPTION OF THE FIGURES

FIG. 1A is a tracing of the inward currents induced by $10^{-7}$M androstadienone (ADO) in a female human VNO cell.

FIG. 1B is a tracing from a cell that was incubated with 100 ng/ml pertusis toxin (PTX) blocking the inward currents.

FIG. 1C indicates when the cells were exposed to ADO (i.e., ADO pulses).

DETAILED DESCRIPTION

Figure 1:
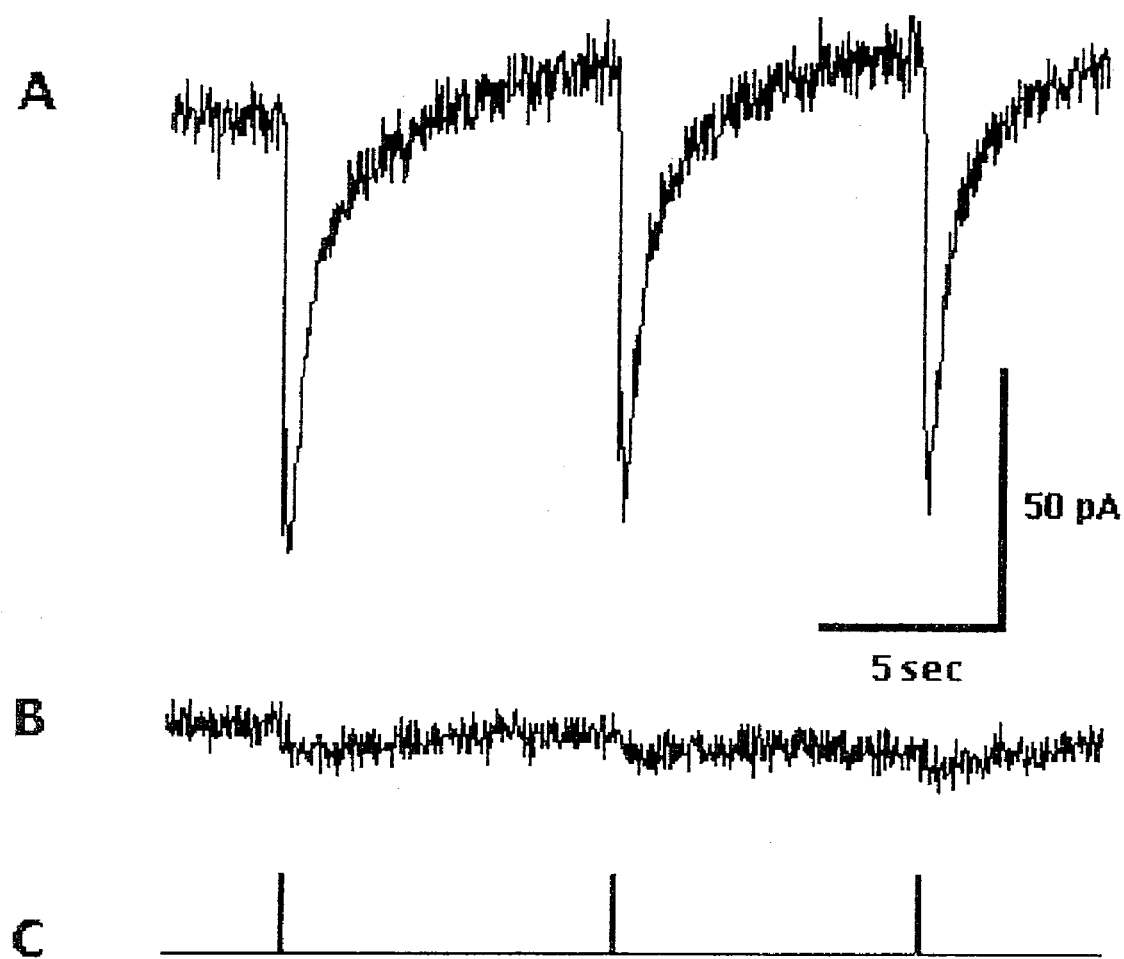
FIG. 1 is an electrophysiological trace showing the effects of pertussis toxin on membrane currents induced by a vomeropherin.

The invention will now be described in detail by way of reference only using the following definitions and examples. All patents and publications referred to herein are expressly incorporated by reference.

The present invention provides a human female VNO-specific cDNA library, which is a unique resource for the identification and isolation of genes expressed in the VNO, specifically genes for pheromone receptors, ion channels and prospective reagents for high throughput assays. Although the human female VNO has been used and is described in detail herein, the male VNO may be subjected to the same methods and procedures to yield a similar cDNA library. Thus, identification and characterization of pheromone receptors, as well as the sexually dimorphic pheromone response, may be investigated.

Definitions

As used herein, the following terms or abbreviations, whether used in the singular or plural, will have the meanings indicated:

A "pheromone" is a biochemical produced by an animal or individual which elicits a specific physiological or behavioral response in another member of the same species. In addition to physiological responses, pheromones can be identified by their species specific binding to receptors in the vomeronasal organ (VNO). Thus, human pheromones bind to human receptors. This can be demonstrated by measuring the change in the summated potential of neuroepithelial tissue in the presence of the pheromone. Human pheromones induce a change of at least about −5 millivolts in human neuroepithelial tissue of the appropriate sex (The binding of pheromones is generally sexually dimorphic.).

Naturally occurring human pheromones induce sexually dimorphic changes in receptor binding potential in vivo in the human VNO. Naturally occurring human pheromones can be extracted and purified from human skin and they can also be synthesized. "Human pheromones" are pheromones that are naturally occurring in humans and effective as a specifically binding ligand in human VNO tissue, regardless of how the pheromone was obtained. Thus, both a synthesized and purified molecule may be considered a human pheromone. Commonly, pheromones affect development, reproduction and related behaviors.

"Sexually dimorphic" refers to a difference in the effect of, or response to, a compound or composition between males and females of the same species.

"Vomeropherin" as used herein is a more general term which includes pheromones and describes a substance from any source which functions as a chemosensory messenger, binds to a specific vomeronasal neuroepithelial receptor, and induces a physiological or behavioral effect. The physiologic effect of a "vomeropherin" is mediated through the vomeronasal organ. Vomeropherins may be naturally occurring compounds, synthetic modifications of natural compounds or totally synthetic compounds.

The term "cDNA library" as used herein refers to a collection of cDNAs representing the messenger RNAs expressed in a cell or tissue type.

"cRNA" means synthetic RNA produced by transcription from a specific DNA template.

A "vector" or "plasmid" is a small circular DNA capable of replicating in a host cell and into which cDNA can be inserted.

Experiments with cultured human VNO neuroepithelial cells show that pertussis toxin (PTX) blocks the electrophysiological response to a vomeropherin in vivo (FIG. 1). PTX uncouples receptors from their heterotrimeric G proteins and thereby blocks signal transduction. Sensitivity to PTX is an accepted marker for pathways involving G protein-coupled receptors that decrease intracellular CAMP, regulate ion channels or activate phospholipases (i.e., couple to $G_i$ or $G_o$). (For a review, see Simon et al., (1991) Science 252:802–808.) We have also implicated a specific type of ion channel in the response of human VNO cells to vomeropherins. These data are entirely consistent with those obtained by Krieger et al. (1999), and thus we provide the first link between a functional G protein-coupled receptor(s) and signal transduction in human VNO cells. However, as noted above, cultured VNO cells are of limited value as a screening tool due to the need to continually isolate new cells. Thus, construction of a cDNA library was desired in order to clone and express pheromone receptors in a cell line.

We constructed a cDNA library of the mRNAs expressed in human VNO tissue and screened it for clones of G protein-coupled receptors with homology to the rat V1R and V2R receptor families and to other G protein-coupled receptor families. Human VNO tissue specimens were collected for this purpose by a team of surgeons. Human VNO RNA is essential for cDNA library construction because: (i) the receptors are species-specific, (ii) the receptors are expressed exclusively in the VNO, and (iii) human genomic DNA contains receptor pseudogenes and introns.

A cDNA library was prepared from the normal human female VNO. In brief, RNA was extracted from pooled VNO specimens and reverse transcribed with SUPERSCRIPT II reverse transcriptase (Life Technologies) to make first-strand cDNA using a Not I-oligo(dT)$_{12-18}$ primer. E. coli DNA polymerase and RNase H were used for second-strand synthesis. Sal I adapters were ligated to the ends and the double-stranded cDNA was digested with Sal I and Not I. The cDNA was directionally ligated into pCMV-Sport7.neo (Life Technologies) and transformed into *E. coli.*

Certain vomeropherins elicit sexually dimorphic responses and some of the receptors are expressed dimorphically. In consideration of these observations, we constructed our first VNO cDNA library with tissue obtained exclusively from human females. Although others have successfully prepared cDNA libraries from individual rodent VNO neuroepithelial cells, we used whole VNO tissue pooled from a number of donors in order to maximize the number, size, and diversity of receptor clones in our library.

The library provides an excellent source to search for novel genes, gene fragments, or other nucleotide sequences encoding proteins that are implicated in detection of pheromones or other vomeropherins in the human VNO. Plasmid vectors are currently available that can accommodate the directional cloning of cDNA such that T7 and SP6 RNA polymerase promoter sequences can be used to generate sense and antisense transcripts for subtractive hybridization and riboprobe synthesis.

Thus, the present invention provides a method of identifying a gene or gene fragment contained within a library of the invention. This method involves the synthesis of at least one unique polynucleotide or oligonucleotide probe sequence comprising a sequence at least partially homologous to a DNA sequence within a selected gene or gene fragment, and of a size to stably hybridize to that gene or fragment thereof. The polynucleotide or oligonucleotide probes may be cRNA, genomic DNA, synthetic DNA, cDNA and the like.

For example, cRNA molecules transcribed from appropriate sequences are useful as hybridization probes in a method for determining the presence or concentration of an oligo- or polynucleotide, e.g. DNA, of interest. Suitable cRNA molecules may be obtained by preparing an RNA molecule complementary to the oligo- or polynucleotide of interest by methods known in the art. According to one method of this invention a labeled cRNA molecule or derivative thereof is contacted with the inventive cDNA library under suitable conditions and for a sufficient period of time permitting complementary nucleotide segments to hybridize. The cRNA molecule or fragment thereof contains a nucleotide segment complementary to the oligo- or polynucleotide of interest. The presence or intensity of radioactivity in hybridized nucleotide segments is then determined and correlated with the presence or concentration of the oligo- or polynucleotide of interest.

Thus, the oligo- or polynucleotide probe is labeled and hybridized to the library of the invention. This label permits the identification of the gene or gene fragment. For example, a probe may be used to identify a nucleotide sequence that encodes a protein related to a VNO receptor.

Any polynucleotide sequence used as a probe and capable of hybridizing to the human VNO libraries of the invention under stringent hybridization conditions (see, Sambrook et al, Molecular Cloning (A Laboratory Manual), 2d edit., Cold Spring Harbor Laboratory (1989), pages 387 to 389) to the DNA sequences of the invention is also covered by this invention. An example of one such stringent hybridization condition is hybridization at 5×SSC at 65° C., followed by a washing in 0.1×SSC at 65° C. for an hour. Alternatively, another stringent hybridization is in 50% formamide, 5×SSC at 42° C.

DNA sequences that hybridize to the sequences of the invention under less stringent hybridization conditions are also encompassed within this invention. Examples of such low-stringency hybridization conditions are 5×SSC at 50° C. or hybridization with 30–40% formamide, 5×SSC at 42° C.

Degenerate primers for known VNO receptors or other family of receptors can be used for the identification and amplification of cDNA's to be analyzed. The technique is carried out through many cycles (usually 20–50) of melting the template at high temperature, allowing the primers to anneal to complementary sequences within the template and then replicating the template with DNA polymerase. PCR can be used to amplify both double and single stranded DNA. The template is mixed with specific or degenerate primers, dNTPs, polymerase buffer including $MgCl_2$, and thermostable DNA polymerase. The template is denatured at high temperature (e.g. 95° C.) and then cooled to a temperature that will allow optimal primer binding. The reaction temperature is then raised to that optimal for the DNA polymerase (e.g., 72° C.) whereby the primers are extended along the template. This series of steps leads to an exponential amplification of the target template.

Screening techniques other than PCR or hybridization are well known to those of skill in the art and the selection of the techniques does not limit the present invention. The procedures for isolating and identifying gene fragments are well known to those of skill in the art; see, e.g. T. Maniatis et al, Molecular Cloning (A Laboratory Manual), Cold Spring Harbor Laboratory (1982).

Once identified and sequenced, the nucleotide fragments of the genes of the invention may be readily synthesized by conventional means, e.g. Merrifield synthesis Merrifield, J.A.C.S., 85:2149–2154 (1963). Alternatively, the DNA may be produced by recombinant methods, then sequenced. Cloning procedures are conventional and are described by T. Maniatis et al, Molecular Cloning (A Laboratory Manual), Cold Spring Harbor Laboratory (1982).

Further, hybridization or PCR methods can be performed using known probes in order to determine whether or not a selected gene is expressed in a gender specific manner by one or more of the libraries of the invention. Genes for which the library is likely to be probed include, but not limited to, for example, pheromone receptors.

As described in the examples below, to date, the results obtained by probing these libraries with neuron and/or neuroepithelial specific probes indicates that the constructed human female library is derived from VNO-specific tissue without olfactory tissue contamination.

Cell Transformation

Cell lines that stably express a VNO gene may be engineered. The inventive VNO receptor gene sequence may be inserted into an expression plasmid comprising a selection marker and suitable regulatory elements, and transfected into a competent host cell. Following the introduction of the plasmid by methods known in the art (for example, calcium phosphate precipitation, electroporation and the like), engineered cells may be allowed to grow for 1–2 days in an enriched media, and then are switched to a selective media. The selectable marker in the novel plasmid confers resistance to the selection and allows cells to stably integrate the plasmid into their chromosomes and grow to form foci which in turn can be cloned and expanded into cell lines. This method may advantageously be used to engineer cell lines that express the desired VNO gene product on the cell surface, and are particularly useful in screening candidate drugs. For example, these cell lines are used to develop automated high throughput screening assays for novel compounds with therapeutic utility in the treatment of psychiatric and endocrine disorders and diseases such as, but not limited to: premenstrual syndrome (PMS), anxiety and phobias, sleep disorders, appetite control, fertility, and hypothalamic-pituitary disorders.

The library of the present invention has been deposited with the American Type Culture Collection (ATCC®), 10801 University Blvd., Manassas, Va. 20110, U.S.A. for patent purposes. The ATCC® accession number of this library is as follows: PTA-1213, and was deposited on Jan. 20, 2000. The deposit of the hybridomas with the ATCC® was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit and for the longer of a) at least five (5) years after the most recent request for the furnishing of a sample of the deposit received by the depositary, or b) for the enforceable life of a patent issuing from the present application. The deposit will be made available by ATTC® under the terms of the Budapest Treaty, and subject to an agreement between Pherin, Inc. and ATCC®, which assures that all restrictions imposed by the depositor on the availability to the public of the deposited material will be irrevocably removed upon the granting of the instant U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14 with particular reference to 886 OG 638).

EXAMPLES

The following preparations and examples are given to enable those skilled in the art to more clearly understand and to practice the present invention. They should not be considered as limiting the scope of the invention, but merely as being illustrative and representative thereof.

Example 1

Tissue Collection

Human VNO tissue specimens were collected for this purpose by a team of surgeons. The human VNO is located bilaterally in the nostrils, and has been associated, inter alia, with pheromone reception. The VNO is a small nasal organ with a central lumen and a pit opening to the nasal cavity. The VNO is a bilateral structure located supra palatial. The pit is approximately 1 to 1.5 mm in diameter and the lumen is approximately 1 to 1.5 cm deep. The lumen is lined with sensory neuroepithelia which constitute a distinct locus of pheromone receptors.

Collaborating otolaryngologists rinsed the human VNO specimens in sterile phosphate-buffered saline (PBS) immediately after resection to remove blood and other fluids. They rapidly excised extraneous tissue and snap-froze the VNO in liquid nitrogen. The frozen specimens were shipped on dry ice to the laboratory for RNA extraction. Thus, authentic VNO tissue specimens were collected under conditions that sought to minimize potential degradation of the RNA.

Example 2

Isolation of a mRNA

Total cellular RNA was extracted from the VNO specimens using Trizol (Life Technologies). This procedure is rapid, and minimizes RNA degradation. However, any method for RNA isolation may be used.

Tissue samples were homogenized in Gibco BRL Trizol Reagent using a glass-Teflon or power homogenizer. After incubation of the homogenized samples for 5 minutes at room temperature to permit the complete dissociation of nucleoprotein complexes, 0.2-ml chloroform was added per 1 ml Trizol Reagent. The samples were mixed vigorously and then centrifuged at 12,000×g for 15 minutes at 4° C. Centrifugation separated the biphasic mixtures into the lower red, phenol-chloroform phase and the upper colorless, aqueous phase.

The RNA was precipitated from the aqueous phase by mixing with 0.5 ml of isopropanol (for each initial milliliter of Trizol Reagent). The samples were incubated at room temperature for 10 minutes and centrifuged at 12,000×g for 10 minutes at 4° C. The supernatant was removed and the RNA pellet was washed once with 70% ethanol. The pellet was air dried and dissolved in diethyl pyrocarbonate (DEPC)-treated water. The RNA was quantitated by $A_{260}$ measurement.

Example 3 cDNA Synthesis

First-strand cDNA was prepared using SUPERSCRIPT II (RNase H⁻) Reverse Transcriptase (Life Technologies) which had been optimized for maximum yield of long cDNA products. The reaction was primed with a Not I-oligo(dT)$_{12-18}$ adapter-primer (Life Technologies) under conditions specified by the supplier. cDNA synthesis was primed by the oligo(dT)$_{12-18}$ at the 3'-poly(A) end of the mRNA; the adapter adds a Not I restriction site to the 5'-end of the first-strand cDNA. The reaction was incubated at 45° C. to melt potential secondary structures in the template mRNA. The length of first-strand cDNA that was synthesized in small pilot reaction mixtures containing $[\alpha\text{-}^{32}P]dCTP$ was determined, relative to known DNA standards, by alkaline agarose gel electrophoresis and autoradiography to test the quality and performance of the materials and conditions.

Second-strand synthesis was catalyzed by E. coli DNA polymerase I in combination with RNase H and E. coli DNA ligase at 16° C. In this procedure, RNase H introduces nicks into the RNA of the mRNA:cDNA hybrids and DNA polymerase I synthesizes second-strands by nick-translation; the low temperature reduces spurious synthesis by DNA polymerase I which has a tendency to strand-displace (rather than nick-translate) at higher temperatures. DNA ligase repairs nicks in the second-strands and improves the yield of long cDNAs. In the final step, T4 DNA polymerase fills in and blunts the ends of the double-stranded cDNA. The double-stranded cDNA was then deproteinized by organic extraction and precipitated with ethanol.

An excess of the commercially available Sal I adapter was ligated to the blunt ends of the double-stranded cDNA from the Not-oligo(dT)-primed reaction. Subsequent digestion with Not I removed the Sal I adapter from one end yielding molecules with a Sal I and a Not I end suitable for directional cloning into a vector that has been double-cut with these two enzymes. The recognition sites for Not I and Sal I are extremely rare in human DNA and thus the double-stranded cDNAs should be cut internally by these enzymes only very infrequently, if at all.

Unligated adapters, low molecular-weight cDNA (<500 base pairs), deoxynucleoside triphosphates, etc. were subsequently removed by chromatography on Sephacryl® S-500 HR prior to ligation into the vector. The >500-bp cDNA was ligated into pCMV-Sport 7.neo (Life Technologies) although any of a number of suitable vectors could be used. This vector has been developed at Life Technologies for cloning SUPERSCRIPT cDNA libraries. Among its features are a selectable marker gene for bacteria (β-lactamase), T7 and SP6 promoters flanking the multiple cloning site for synthesis of single-stranded sense and anti-sense cRNAs, a cytomegalovirus (CMV) promoter and SV40 polyadenylation signal for eukaryotic expression of directionally cloned inserts, and a selectable marker gene for eukaryotic cells (neo$^r$).

The double-stranded cDNA from the Not-oligo(dT)-primed reaction with Sal I and Not I ends was directionally cloned into pCMV-Sport 7 that had been cut with these two enzymes. After ligation to the vector, the DNA was transformed into a highly competent strain of E. coli such as DH10B (Life Technologies). Recombinants were selected on LB agar plates for resistance to ampicillin. The library was amplified as described in Example 4 and plates prepared for colony hybridization.

Example 4

Amplification of Primary Library

The primary library was amplified once under semi-solid conditions. Semi-solid amplification of primary cDNA transformants minimizes representational biases that can occur during the expansion of plasmid cDNA libraries.

Media Preparation

2×LB: 20 g Trptone, 10 g Yeast Extract, 10 g NaCl in 1,000 mls H$_2$O.

2×LB Glycerol (12.5%): 175 ml 2×LB, 25 ml Glycerol (100%). Filter sterilize and store for up to two months at room temperature.

Prepare 2 liters of 2×LB. Remove 200 mls of the 2×LB to make the 2×LB Glycerol. Place a large stir bar and 1.35 g SeaPrep (FMC) agarose into each of four 500-ml autoclavable bottles. Place bottles on stir plates. With the stir plate turned on, add 450 ml of 2×LB to each bottle, avoiding the formation of large clumps of agarose. Autoclave these bottles of 2×LB agarose for 30 min. Cool bottles in 37° C. water bath for approximately 2 hours until media reaches 37° C. After the media reaches 37° C., add Carbenicillin to 50 μg/ml (preferred antibiotic) or Ampicillin 200 μg/ml. Mix on stir plate.

Amplification

Briefly, 4×10$^5$ to 6×10$^5$ primary cDNA transformants (colonies from original library) were added to each of the autoclaved bottles of 2×LB agarose and mixed thoroughly on a stir plate for 2 minutes. The caps were tightened and the bottles placed in an ice water bath (0° C.) such that the level of water in the bath is at the same level as the upper level of media in the bottle. The bottles were incubated for 1 hour in the ice bath. The bottles were gently removed from the ice bath and the excess water wiped off the outside of the bottles. The bottle caps were loosened and the bottles placed in a gravity flow incubator set at 30° C. The bottles were incubated for 40–60 hrs without disturbance.

Cell Harvest

The contents of the bottles were poured into GSA bottles and centrifuged at 8,000 rpm for 20 minutes at room temperature (Caution: Make sure that the rotor was set at room temperature for at least two hours before adding the GSA bottles. Rotors at 4° C. will cause solidification of agar.) The supernatant was decanted off and the cells resuspended in a total volume of 100 ml 2×LB Glycerol (12.5%). Two 100 μl aliquots were removed for plating, further analysis, and colony estimate. Cells were filtered through sterile cheesecloth to remove agarose clumps if present.

Cell Storage

The cells were subdivided into small aliquots (Note: It is useful to make a number of 1 ml and 100 μl aliquots.) and stored at −70° C. Frozen cells can then be used to prepare DNA for experiments or can be further amplified in liquid at 30° C. to obtain DNA. Use 2.5×10$^9$ cells per 100-ml growth medium for further expansion of library.

Amplified Library

The amplified library contains ~3.5×10$^{11}$ colony-forming units (CFU) representing ~1×10$^7$ primary transformants. Inserts range from ≧300 to >3000 base pairs (bp) in length, with an average insert size of ~1500 bp. For comparison, mRNAs in the rat V1R receptor family contain, on average, ~915 bases in the open reading frame (ORF) and ~230 bases in the 3'-untranslated region (UTR) (Dulac and Axel, 1995). Therefore, the inventive cDNA library will be a source of suitably sized clones for identification and characterization of numerous genes and gene fragments. We also point out that full-length cDNAs containing the precise 5' end of the mRNA sequence, though scientifically interesting, are not essential provided that we obtain the entire full-length ORF (see below).

Example 5

Probes (i) We designed PCR primer pairs based on the published sequences of the rodent VNO receptors using readily available software packages such as Oligo™ or Primers. Biosource (Foster City, Calif.) synthesized the primers on a standard "fee-for-service" basis. The primers flanked the region encoding transmembrane domains II through VI of the rat receptor sequence that does not appear to contain introns. A separate PCR reaction was set up for each primer pair and the target region amplified from commercially available rat genomic DNA (Clontech). The products were analyzed by agarose gel electrophoresis to assess size and purity. If necessary, products of the predicted size were gel-purified to remove any spurious species. The PCR amplicons were analyzed by restriction enzyme mapping and/or sequenced on a "fee-for-service" basis by ACGT, Inc. (Northbrook, Ill.); they were cloned into a suitable vector such as pGEM-T-Easy (Promega). This procedure was also used for human "VN6", a sequence from GenBank, probably a testes cDNA, and for HG25X, a human VNO receptor pseudogene.

Each probe was labeled to high specific activity by including [α-$^{32}$P]dCTP in the RediPrime (Amersham) random-priming reaction. The specificity and identity of the labeled rodent PCR products was confirmed by Southern blotting, at low (55°) or high (68° C.) stringency, to restriction enzyme-digested rat genomic DNA and compared to the published hybridization pattern(s) for that clone. These PCR products were also separately hybridized to blots of human genomic DNA (Clontech) at low or high stringency to ensure that they successfully cross-hybridize to human sequences under the conditions used. The human PCR amplicons were tested by separately hybridizing each to blots of human genomic DNA at low or high stringency prior to use in screening the library.

(ii) We used short oligonucleotide probes based on regions generally conserved in G protein-coupled receptors to screen the library (Kel et al., 1998). We screened the library by colony hybridization using a mixture of 15 short oligonucleotides that should detect conserved sequences in most, if not all, G-protein coupled receptors. This varies from standard colony hybridization because the probes are very short, i.e., 8 nucleotides, and do not represent any specific mRNA sequence. The probes were labeled at the 5' end with [$^{32}$P]-ATP and hybridized at 4° C. followed by washing at 10° C. Clones PP40 and PP41 were isolated from this screen.

(iii) We designed degenerate PCR primers for the V2R family based on Cao et al. (1998) and for olfactory and taste receptors. The pairs of degenerate oligonucleotide primers based on conserved regions of the known receptors (e.g., within the first and third intracellular loops of the V2R family). These oligos were used to prime PCR on the amplified library to screen $G_O$-coupled receptors. The resulting amplicons were sequenced to identify receptor fragments and then used to screen the VNO cDNA library.

Example 6

Characterization of Amplified Library

The library was screened for the presence of cloned cDNAs representing proteins whose expression in the human VNO has been determined by immunohistochemistry. Oligonucleotide primer pairs were designed based on the GenBank mRNA sequence for each of the proteins and were used to direct PCR with ~$10^7$ CFU from the amplified library as the template. When a unique band of the predicted size was detected by ethidium bromide staining of an agarose gel (Table 1) the results were scored positive. The PCR products can be restriction mapped and/or sequenced, if necessary, to confirm their identity. In each case, a parallel reaction containing the primer pair alone, in the absence of template, did not yield any significant PCR products.

TABLE 1

| Protein | Immuno | PCR[a] |
|---|---|---|
| Neuron-specific enolase | + | + |
| Protein gene product 9.5 | + | + |
| Olfactory marker protein | − | − |
| Synaptophysin | + | + |

[a]1 cycle: 94° C./5 min; 30 cycles: 94° C./15 sec, 58° C./30 sec, 72° C./45 sec; 1 cycle: 72° C./10 min.

The data in Table 1 show that the library contains cDNA for proteins identified immunohistochemically in sections of intact human VNO. Thus, the inventive library displays characteristics consistent with those seen in the intact tissue.

Example 7

Protein Identification in Human VNO cDNA Library

As noted above, in vivo data (FIG. 1) indicate that cells isolated from the VNO of human volunteers respond electrophysiologically to a vomeropherin via a PTX-sensitive pathway, a hallmark of G protein-coupled receptor signaling. Thus, we anticipated that components of the pathway such as G proteins (e.g., $G_i$ and $G_0$), adenylyl cyclase (e.g., type 3 and 7), and various ion channels are expressed in these cells. We assayed for expression of these proteins in the VNO by screening our library for cDNA clones of the corresponding mRNAs. Knowledge of the signaling components expressed in VNO neurons is essential to express the receptors functionally in tissue culture cells for high throughput drug screening assays.

The library was screened by PCR using primers for various known mRNAs to assess the signal transduction mechanism of the activated VNO receptor. The primers used for screening were generated from known sequences for either the human or rodent miRNA. The PCR primer pairs can be specific for individual mRNAs, such as $G_i$ or $G_O$, or degenerate to allow simultaneous amplification of related sequences in the same family. Clones of amplicons obtained with a unique primer pair were sequenced directly. Clones of amplicons obtained with degenerate primers were distinguished by restriction mapping and representatives sequenced. BLAST analysis was used against GenBank to identify the sequences that were obtained and thereby learn about signal transduction mechanisms in the VNO.

The results of the screening are shown in Table 2. The cDNA library was positive for adenylyl cyclase type 2, 3 and 7, G$\alpha$i1, 2 and 3-proteins, and Golf. These results show the presence of the Golf protein although this G-protein is thought to be uniquely associated with olfactory tissue and is not detected in rodent VNO. However, OMP is not detected in the inventive cDNA library. Thus, the Golf did not arise from contaminating olfactory tissue and may couple to novel receptors in the human VNO. Also of interest is the failure to detect G$\alpha_O$. Based on work on the rodent receptors, the G$\alpha_O$ was expected to be present if there is a V2R human homolog. The lack of detection of the G$\alpha_O$ may indicate that the human V2R homolog utilize a G-protein other than G$\alpha_O$. Other explanations also exist.

Example 8

Screening for Receptor cDNA

We separately screened the cDNA library for clones that hybridize to the V1R probes. Pools of $^{32}$P-labeled probes were hybridized at low stringency to nylon membranes containing ~3×$10^4$ colonies. The filters were successively washed at low stringency, autoradiographed, washed at high stringency, and autoradiographed. Clones that were positive after each round of washing were identified, plated to yield single colonies, and retested to eliminate false-positives and to ensure purity.

The size of the insert in positive clones was determined after release from the vector by restriction enzyme digestion with NotI and SalI. We initially selected the longest positive clones for further analyses. If the clones were deemed too short to contain a full-length open reading frame (ORF) (based on comparison to the rodent cDNAs), we can use one of several approaches to obtain the complete cDNA: As noted above, the coding regions of the rodent V1R VNO receptors do not contain introns. Therefore, it is possible to screen a commercially available human genomic library at high stringency using a probe derived from the 5' end of a human receptor cDNA. We can identify overlapping genomic clones that extend the sequence upstream toward the 5' end, and subsequently assemble plasmids containing the full-length ORF.

Alternatively, we can use one of various published methods of 5'-RACE to extend the cDNA clones toward the 5' end. We do not need clones containing the precise 5' end of the mRNA sequence to express the receptors, provided that we obtain the full-length ORF.

Alternatively, a randomly primed human VNO cDNA library is prepared. Mixed hexamers randomly primed first-strand cDNA synthesis along the poly(A)$^+$ human VNO mRNA; the reactions are incubated at 45° C. to melt potential secondary structures in the template mRNA. Second strands are synthesized using *E. coli* DNA polymerase I in combination with RNase H and DNA ligase as was done for the oligo(dT)-primed VNO cDNA library. In the final step, T4 DNA polymerase fills in and blunts the ends of the randomly primed double-stranded cDNA. The cDNA is ligated to an excess of commercially available Eco RI (Not, Sal) adapter. The adapter contains the recognition sites for Not I and Sal I to facilitate subsequent excision of the insert from the vector. (These enzymes will cut the cDNA inserts only infrequently, if at all.) The randomly primed double-stranded cDNA is non-directionally cloned into a suitable vector that has been linearized with Eco RI and treated with phosphatase. The ligated DNA is transformed into competent *E. coli* DH10B. The randomly primed library is screened at high stringency using a probe derived from the 5' end of individual human receptor cDNAs to identify overlapping fragments that can be assembled into a full-length cDNA clone.

Example 9 cDNA Clones Isolated from the Human VNO cDNA Library

The cDNA library was screened using probes based on published rat VNO receptors, human homolog of rat VN6 and human HG25x pseudogene sequences. See SEQ. ID Nos 7–15. Probes were hybridized with clones under low stringency conditions to maximize the number of possible candidates for the human VNO receptor. Table 3 summarizes a partial listing of the clones sequenced, their putative homolog based on known gene sequences from GenBank, and the homology between the isolated sequence and the homolog, i.e., known GenBank sequence. At least six novel sequences were identified. See SEQ ID No. 1–6, and 16–20.

TABLE 2

| Protein | Rodent OE | Rodent VNO | Hu VNO cDNA library | Hu VNO Method |
|---|---|---|---|---|
| Adenylyl cyclase type 2 | | + | + | PCR/sequence (PP23) |
| Adenylyl cyclase type 3 | + | + non-neural cells | + | PCR/sequence (PP24) |
| Adenylyl cyclase type 7 | | + | + | PCR/sequence (PP39a) |
| $G_{\alpha 11}$ | | + | ND | |
| $G_{\alpha 13}$ | | + | – | PCR |
| $G_{\alpha 14}$ | | + | – | PCR |
| $G_{\alpha i1}$ | | – | + | PCR/sequence (PP18; PP20) |
| $G_{\alpha i2}$ | + | + | + | PCR/sequence (PP14a) |
| $G_{\alpha i3}$ | | – | + | PCR/sequence (PP16a; PP17a) |
| $G_{\alpha o}$ | + | + | – | PCR |
| $G_{\alpha q}$ | | + | ND | |
| $G_{\alpha s}$ | | + | ND | |
| $G_{olf}$ | + | – | + | PCR/sequence (PP15a; PP15b) |
| Neuron-specific enolase | | | + | PCR |
| OMP | + | + | – | PCR |
| PGP9.5 | | | + | PCR |
| Synaptophysin | | | + | PCR |
| Trp2 | | + | – | PCR |
| Trp homologs | | | – | PCR |

ND, Not done
–, Not detected

TABLE 3

| Clone | Homolog | Function of homolog | Comments |
|---|---|---|---|
| PP21 | human cDNA NM003944 (1428 bp) mouse cDNA AI573970 | human selenium binding protein mouse acetaminophen binding protein | bp 54–897 95% identical to 587–1424 of human homolog |
| PP22 | human fetal kidney HSM800147 (1199 bp) | similar to RING Zn finger proteins | bp 370–667 98% identical to 1–298 of homolog |
| PP26 | human brain cDNA AB011108 (6680 bp) | related to serine/ threonine protein kinases | bp 13–643 97% identical to 3476–4102 of homolog |
| PP27 | | | SEQ ID No. 18 |
| PP28 | | | SEQ ID No. 19 |

TABLE 3-continued

| Clone | Homolog | Function of homolog | Comments |
|---|---|---|---|
| PP29 | human Ciz1 mRNA AB030835 (5936 bp) | | bp 282–593 99% identical to 249–560 of homolog. bp 1–281 not in homolog. Unspliced? splice variant? SEQ ID No. 20 |
| PP30 | human erg2 M17254 (3166 bp) | transcription factor; protooncogene | ~600 bp sequenced; identical |
| PP31 | human erg2 M17254 (3166 bp) | transcription factor; protooncogene | ~550 bp sequenced; identical |
| PP32 | | | NOVEL; ~600 bp @5'; ~500 bp @3'; SEQ ID Nos. 1 and 2 |
| PP33 | | | NOVEL; ~600 bp @5'; SEQ ID No. 3 |
| PP34 | human melanoma adhesion molecule NM006500 (MCAM) (3583 bp) | cellular adhesion | ~600 bp sequenced; identical |
| PP35 | human umbilical vein endothelial cell EST AA296414 (270 bp) | | partial match: 145 bp match of ~1100 sequenced; SEQ ID No. 4 and 5 |
| PP36 | | | NOVEL; ~1000 bp @5' sequenced |
| PP38 | | | NOVEL; ~500 bp @5' sequenced; SEQ ID No. 6 |
| PP40 | human PAC clone RP5-1093o17 (160687 bp) | genomic DNA clone | NOVEL cDNA; ~660 bp @5' end sequenced; bp 17–474 98% identical SEQ ID No. 16 |
| PP41 | human ubiquitin-conjugating enzyme; AF085362.1 (1294 bp) | ubiquitin-conjugating enzyme | NOVEL cDNA; ~550 bp sequenced; bp 296–431 85% identical to be 276–410 of homolog; SEQ ID No. 17 |

Example 10

Sequencing

Single-stranded sequencing of selected (full-length) clones was done by standard methods. Oligonucleotides that are complementary to the T7 and SP6 promoters in the pCMV-Sport7.neo vector were used to prime sequencing reactions from each end of a cloned insert. Internal primers, based on newly acquired sequence data, were synthesized, as necessary, to sequence overlapping internal regions of the cloned cDNAs.

We examined the assembled sequences by computer for the presence of a potential full-length open reading frame. Clones containing an in-frame internal termination codon were excluded because they likely represent expressed pseudogenes. We used standard BLAST analysis to compare the human VNO clones to each other and to sequences in GenBank. Based on cross-hybridization to rodent VNO receptor cDNAs (used to screen the library) and our proprietary PTX data, the human VNO clones show homology to the superfamily of G protein-coupled receptors and have seven predicted transmembrane domains. By virtue of the selection method, they also fall into subfamilies with homology to either the rodent V1R or V2R family of receptors. Analysis of the lengths of the extracellular N-terminal domains determine if the differences between the rodent V1R and V2R families are conserved in humans.

Example 11

In Situ Hybridization

Confirmation that the cloned receptors and components of the signal transduction cascade (identified by PCR) are expressed in the neuronal cells of the human VNO is by in situ hybridization as described in detail by Schaeren-Wiemers and Gerfin-Moser (1993). This approach also provides important information about the number and distribution of cells expressing these genes in the VNO. Human VNO tissue is fixed with Tissue-Tek embedding medium (Miles) immediately after surgical resection and frozen at −40° C. in 2-methyl-butane. Sections (15 μm) are cut on a cryostat, mounted on polylysine-coated slides, and processed as described (Schaeren-Wiemers and Gerfin-Moser, 1993).

Digoxigenin (DIG)-labeled sense and anti-sense cRNA probes are transcribed from the linearized pCMV-Sport7.neo cDNA clones in vivo using SP6 and T7 RNA polymerase, respectively, in the presence of DIG-11-UTP (Roche Molecular); cRNA probes transcribed from the 3'-untranslated region should offer the highest degree of specificity (Ryba and Tirindelli, 1997). We will determine the size of the DIG-labeled cRNA probes and confirm their detection prior to use for in situ hybridization as follows: The cRNA is electrophoresed in a 1% agarose gel containing formaldehyde and ethidium bromide. The 18S and 28S ribosomal RNAs present in the unbound fraction from the oligo(dT)-cellulose column (see above) can be run in a parallel lane as size standards and visualized by UV transillumination.

The gel is blotted overnight onto a nylon membrane (Zeta Probe membrane; BioRad) in 10×SSC, pH 7.0, rinsed in 2×SSC and fixed by UV cross-linking. After blocking non-specific sites on the membrane with Blocking Reagent (Roche Molecular), the transferred DIG-cRNA is bound to sheep anti-DIG Fab antibody fragments coupled to alkaline phosphatase (Roche Molecular), and detected by color reaction using 4-nitroblue tetrazolium chloride and 5-bromo-4-chloro-3-indole-phosphate. The size of the cRNA transcripts will subsequently be reduced to ~200 bp by limited alkaline hydrolysis prior to in situ hybridization as recommended by Schaeren-Wiemers and Gerfin-Moser (1993); the size reduction can be confirmed by gel electrophoresis and blotting as described above.

VNO tissue sections on slides are prehybridized in a buffer containing yeast RNA and herring sperm DNA (Roche Molecular) at room temperature for at least 6 hr. The buffer is replaced with a hybridization buffer containing DIG-labeled probe and hybridized overnight at 72° C. (Schaeren-Wiemers and Gerfin-Moser, 1993). Hybridized DIG-labeled probe is detected with anti-DIG antibodies coupled to alkaline phosphatase (Roche Molecular) and color reagent. The sections are counterstained with Hoechst 33258, which stains nuclei, and examined by light microscopy.

Each anti-sense cRNA receptor probe hybridizes specifically to a small number of neuroepithelial cells distributed through the human VNO section. In contrast, the corresponding sense cRNA probe yields no distinct signal when hybridized in parallel to an adjacent serial section, thus ruling out non-specific hybridization to RNA or hybridization to genomic DNA. Probes for components of the signal transduction cascade will vary in the number of cells to which they hybridize. For example, anti-sense probes for specific G proteins (e.g., $G_i$) that are detected in the cDNA library hybridize to a subset of neurons in the tissue section, whereas anti-sense probes for adenylyl cyclase(s) and ion channels hybridize to many or all neurons. These results confirm the expression of the cloned sequences in the VNO, identify the cell type(s) expressing these proteins, and provide insights into gene expression and signal transduction in this tissue.

Example 12

Tissue Specificity

The tissue-specificity of the cloned receptor cDNAs is assessed by northern blot hybridization. Commercially prepared multiple tissue northern blot membranes containing mRNA isolated from a spectrum of human tissues (Clontech) are hybridized at high stringency (42° C.; 50% formamide) to one or a mixture of $^{32}$P-labeled VNO receptor probes. The probes are prepared by random-priming (RediPrime) the human cDNAs in the presence of $[\alpha\text{-}^{32}P]dCTP$. It is essential to include a hybridization control in these experiments. The rodent VNO receptor probes do not hybridize at high stringency to mRNA isolated from other tissues (Matsunami and Buck, 1997), and the commercially available human multiple tissue northern blots do not contain VNO mRNA. We, therefore, include a $^{32}$P-labeled probe for a common housekeeping mRNA such as human GAPDH in each hybridization. This control confirms that the conditions are adequate to detect hybridization and simultaneously verifies the quality and relative quantity of mRNA in each lane of the blot.

Within the limits of sensitivity, the multiple tissue northern blots define the profile of receptor expression in the tissues tested. Higher sensitivity can be obtained by RT-PCR, but this procedure requires sufficient sequence information on every clone to design specific primers, and template mRNA from many different human tissues.

CONCLUSION

We detect cloned cDNAs in our library by PCR for the 3 proteins that are detected by immunohistochemical staining of human VNO tissue sections. We do not detect OMP cDNA in the library and Takami et al. (1993) do not detect the protein in human VNO tissue sections by immunohistochemical staining, even though it is present in the rodent VNO. We obtain negative PCR results for OMP using several independent samplings of the library, whereas we always obtain a product of the predicted size when human genomic DNA (Clontech) is used as template with these primers in a parallel reaction. Because the OMP mRNA contains a very long 3'-UTR, we have also tested a second primer pair, designed to amplify a region adjacent to its 3'-poly(A) tail. This primer pair also does not amplify OMP cDNA sequences from the library but, nonetheless, amplifies a region of the predicted size using human genomic DNA as the template in a parallel reaction. The apparent absence of both detectable OMP protein and cDNA makes it unlikely that this is simply a failure to clone the mRNA. We draw these conclusions: (i) our library contains cloned cDNAs for proteins expressed in neuronal/neuroendocrine cells; (ii) absence of OMP cDNA implies that the neuronal/neuroendocrine cDNAs are not derived from olfactory neurons which abundantly express this protein; (iii) the agreement between the PCR and immunohistochemistry suggests that the library reflects gene expression in the human VNO; (iv) the absence of detectable OMP cDNA and protein likely represents a real species difference between humans and rodents.

Although the foregoing invention has been described in some detail by way of illustration and example for purposes of clarity and understanding, it will be obvious that certain changes and modifications may be practiced within the scope of the appended claims.

The invention claimed is:

1. A human vomeronasal organ (VNO) cDNA library deposited with the American Type Culture Collection (ATCC) under Accession No. PTA-1213 constructed from human female VNO tissue.

2. A human cDNA library of female VNO tissue comprising cDNAs of sequences comprising SEQ ID NO: 1, SEQ ID NO: 2, SEQ ID NO: 3, SEQ ID NO: 4, SEQ ID NO: 5, SEQ ID NO: 6, SEQ ID NO: 16, and SEQ ID NO: 17.

3. A human cDNA library of female VNO tissue of claim 2 comprising cDNAs encoding Gα proteins $G_{i1}$, $G_{i2}$, $G_{i3}$ and $G_{olf}$, and lacking cDNAs encoding $G\alpha_o$ proteins.

4. A human cDNA library of female VNO tissue claim 2 comprising cDNAs encoding adenylyl cyclase types 2, 3 and 7.

\* \* \* \* \*

SEQUENCE LISTING

<160> NUMBER OF SEQ ID NOS: 20

<210> SEQ ID NO 1
<211> LENGTH: 651
<212> TYPE: DNA
<213> ORGANISM: Homo sapiens

<400> SEQUENCE: 1

```
gtcgacccac gcgtccgaag tgagaccctg tcttgaaaaa aaaaaaaatt aaccaatatg      60
attaataata atggcagcat caagagcctg tacttcctat gtgtttccat gtgtgtaaat     120
gctctgtcac accgtctcat ttcacctcat ttccccataa agaacattct attaactggg     180
```

-continued

| | |
|---|---|
| gttcagagag taacttgttc tgtcgctcac ccaagatcgc cgtgtggttc ccgagtgtaa | 240 |
| ggtgtgaagc caagtctctg tggccctggg gcccgagccc tcaactgccc tgctagggtc | 300 |
| caagctgacc actgcagggc cttagtctgg aggaacggct tgactccgga catctgcagg | 360 |
| agtgtttgct gtgttgagtt gagcccctct gccagacgtg tcaaaacaaa tgcttttgtg | 420 |
| tgtttactgc ctcacacgct cagccagaag ctcctgtttt atcatctagt ttagattgag | 480 |
| gggaagaggc ttcatcagta aggacctgtc tcactcttca tcccacggcc ctgggccatg | 540 |
| ccctgttagc ttcaagaagc agttatcctc agggtggtcc tgctcaggct gccccacccc | 600 |
| atcctgtgtc tgcgccagat atgtagattg atttcagtcg ctttatgcta a | 651 |

<210> SEQ ID NO 2
<211> LENGTH: 469
<212> TYPE: DNA
<213> ORGANISM: Homo sapiens

<400> SEQUENCE: 2

| | |
|---|---|
| ttttttttttt tttttaaatg gagtttcgct tttgttgccc aggctggagt gcaatggtgt | 60 |
| gatctcggct caccacaacc tccgccttac actgtttatc acgagggaga caagtggaga | 120 |
| accttggaaa tgtaaaggaa gatgagccca cgcctttcaa agagaaagag ccggagcagg | 180 |
| gaaaccctga tcgtggctaa ttggcccatc agggtcctgc cctggacaga cctaggtgag | 240 |
| ggcgtctttta aagaaaacgt cccacctccg cttgccacag agatttctaa ggtttgccca | 300 |
| ctgtcctttt gtaagtgcct gctgggtaag tgtggagata agatgagtat tacattatga | 360 |
| tgcttcctca tgcatgaaac tctgttttaa agagagtctg gaggggccca tcaggaaggg | 420 |
| agagcctgac cagtggaggt agaaggaagg ctgctttatt aagagaagt | 469 |

<210> SEQ ID NO 3
<211> LENGTH: 604
<212> TYPE: DNA
<213> ORGANISM: Homo sapiens

<400> SEQUENCE: 3

| | |
|---|---|
| gtcgacccac gcgtccgagc ttttatggca gtgccccgtt ggcctactga taagaaaccg | 60 |
| tggctgctca ggcggctgct gcacctgctg cttttgccgt ttctttcctg cttgtgtaga | 120 |
| taaagccctg cggagctgag ctggtttcac cttcgtcatt acaactttga agccctctgg | 180 |
| aggctttaac aacatcttgc cagtcttatc ctagagagga cagctagttc tccttgctag | 240 |
| gtgggaaggc tgaagctgaa cttgggaatt ctcatcaggg ctgcccatag gaggtctcat | 300 |
| catttccagc agaggaaaga aacttgaaga aagaatggat ttaagtaatt gcctccaggc | 360 |
| agtcttctct ctctcctccc tctctttaaa aaaaatcatg ggatcatgta attttttcagc | 420 |
| ataaataatg gcaataatgg ttggaggaca aggtaagatt tctggaaatc tggcaactac | 480 |
| gcaggtgact caaaagaaaa aataatgacc aagctaatct ttaactccac acctactctt | 540 |
| gccttttccc aggcagcttt cctggttttta agagcaaggg ttccccaaac ctgcagtagg | 600 |
| tatc | 604 |

<210> SEQ ID NO 4
<211> LENGTH: 666
<212> TYPE: DNA
<213> ORGANISM: Homo sapiens -continued

```
<400> SEQUENCE: 4
gtcgacccac gcgtccgggg actcttcaca cagctttcta gtccattccc aggaccactg      60
ggtacctgtc agttggcctg taaggaagtg aagggtgggg acacagaggc atgtgtcacg     120
ttcacttaga tcctcactga ccaaaaggca ggagggtttc cttaggaaac aatgtaaact     180
tgttttctat tggggtataa aatccacctc aggccagtgg ttattctcga tcaagtgggc     240
tccaggaggt ctgtctgtca gtattaagtg aaatgagagc ctcccctcca ggcctggccc     300
ccagtccggc ctcgcacccc tttcctgcc caccctcatg ttttggtct ttggctcatg      360 actgcaccgt ctcaccatgc tcttgtcccc ttccttgcag gatgatgcta tatttgggat     420
ccttaacaaa gtgaagcctt cctataaatc ctgtgccgac tgcatgtacc ctacagccag     480
cggggctctg aggcctccag ggagcgatgt gaggacccca atgctcccgc catctgcacc     540
cagccagcct ttctacccca catcacgtcc tcccctgtgg cccacttggc agcaggtcc      600 gtgttccgga gaagccagcc tctggcccaa ccaaccttcc ccgttcctta ccaccagcag     660
gctcca                                                                666

<210> SEQ ID NO 5
<211> LENGTH: 755
<212> TYPE: DNA
<213> ORGANISM: Homo sapiens

<400> SEQUENCE: 5 ttttttttt tttttacaa ctccttaaaa aggtaaaagc catcgcttga gccagggagg      60
ttgatgctgc agtgagtcat gattgcacta ctgtactcca gcctaggtga cagagccagg     120
ccctgtctta aagaggaaaa accattccta gctcacgggg ccacatgcca tagtttgctg    180 accctgaat tcaaccttt tgcttttctg caagctgcct ctctctcgaa atgttttgac      240
atctagcttg ctgacacctt tgattcaagc ctggcgcagc gggactggct gagctcacct    300
gagtcttaaa ggggccgccc acagagccag gcagcgacta cagatccctc ttatactccc    360
tcactgctgc tgggaagagc tggagggaaa caggaagcag taatctcact gcaggaaggg    420
gcaactgtag acatccggga agcatcccga cagtcccgtt cctttcgggg aagccgctga    480
aatctccttt cccttcccta gatgggcct agtggaccta agcatctggg ctctcagcag    540
gacgatgtgt ctcagaacca ccacctgagc cagacacttg agcaatttca acctaaaca    600 caatcatgtg tttcagcagc agacactcaa caatgcaggg tgggcccttc cccttgagat    660
ttaaacttca gcattagcaa caactggaaa caacccatac attttccca ccgggacccc     720 tgtgctggtc aaacccgtta caacacacca ggaca                               755

<210> SEQ ID NO 6
<211> LENGTH: 445
<212> TYPE: DNA
<213> ORGANISM: Homo sapiens

<400> SEQUENCE: 6
agcaggctgg taccggtccg gaattcccgg gatatcgtcg acccacgcgt ccgtattttt     60
atgagtgcag tttacagtcc acaggtatat tctttgtcac ttaactacag caaattcttg    120
atcattctct ttagaaaagt ctcagaaatc atggcacctt gaaatgggaa acatttcatt    180
agtaattttg gatgcaaact gctttcctgt gttcacagaa tgggcagagg tggaaccgtt    240
aacaccactt ccctctttag tgacttccat gccatcacca tcagtgtgac tcaagtaggt    300
tagtgcagca gaaatttcag tgacacttat aataataaaa aaaataaatg gagatcagcc    360
```

| | |
|---|---|
| aaatgaaaac aagaaatgac tatgtatttt agctttgccc taggagggga attagccacc | 420 |
| atcacttatg tttggtggag actca | 445 |

<210> SEQ ID NO 7
<211> LENGTH: 405
<212> TYPE: DNA
<213> ORGANISM: Homo sapiens

<400> SEQUENCE: 7

| | |
|---|---|
| gtccagttat ctacaggtac aggttgatga gaggcctctc catttccacc acctgcctgt | 60 |
| tgagtgtcct ccaggccatc aacctcaccc caaggagctc ccgtttggca atgttcagag | 120 |
| atcctcacat cagaaaccgc gttgctttct cttgctgtgg gtcttccaca tatccattag | 180 |
| tggaagcttc ttagtctcca ctcttccctc caaaaatgtt gcctcaaata gtgttacatt | 240 |
| tgtcactcaa tcctgctctg ctgggcccct gagttgcttc cttgggcaga caattttcac | 300 |
| actgatgaca tttcaggatg tctccttgca gctcatggcc cccttcagtg gatacatggt | 360 |
| gattctcttg tgcaggcata acaggcagtc tcagcatctt catag | 405 |

<210> SEQ ID NO 8
<211> LENGTH: 414
<212> TYPE: DNA
<213> ORGANISM: Homo sapiens

<400> SEQUENCE: 8

| | |
|---|---|
| gaagtgagga gcaccagagg actgatcacg gcatagacat tgactacaag actctgaact | 60 |
| tgctggttga ttgggccata tgcccacaac attgctgagg agaaggagat gatgaaatcc | 120 |
| acccaacaga ggaccacaga gaaacttacc agcagcagta tggtctggat ggcccgtttc | 180 |
| tcaggggaag ctcctgggga aggaccattg ctgtgaaggt ggtgggatca cctctgaggc | 240 |
| ctgaataaga gagtcaccat gtatgcaatt aagaacagca gtattcctac caggaaagca | 300 |
| tccctaagtg ttgtcagaat aagaaacgtg gccctgagga tgaagctcat ggagaaaact | 360 |
| gagcagtact tacctatatt cagtacattt gtctggctca cctggaagca gcta | 414 |

<210> SEQ ID NO 9
<211> LENGTH: 632
<212> TYPE: DNA
<213> ORGANISM: Rat VNO receptor

<400> SEQUENCE: 9

| | |
|---|---|
| tgcccattgg tctcttgtcc ctaatcaact tactatgct actgatgacg gcattcatag | 60 |
| ccacagacac ttttatttct tggagagggt gggatgacat catatgtaaa tcccttctct | 120 |
| acctgtacag aacttttaga ggtctctctc tttgtaccag ctgcctgttg agtgtcctgc | 180 |
| aggccatcat cctcagtccc agaagctcct gtttagcaaa gttcaaacat aagccttccc | 240 |
| atcacatctc ctgtgccatt cttctctga gtgtcctcta catgttcatt agcagtcacc | 300 |
| tcttagtatc catcattgcc accccaaatt tgaccacgaa tgactttatt catgttactc | 360 |
| agtggtgctc tattctaccc atgagttacc tcatgcaaag catgttttct acactgctgg | 420 |
| ccatcaggga tgtctttctt attagtctca tggtcctgtc aacatggtac atggtggctc | 480 |
| tcttgtgtag gcacaggaaa cagacccggc atcttcaggg taccagcctt tccccaaaag | 540 |
| catccccaga acaaagggcc acccgttcca tcctgatgct catgagctta tttgttctga | 600 |
| tgtctgtctt tgacagcatt gtctgcagct ca | 632 |

<210> SEQ ID NO 10
<211> LENGTH: 628
<212> TYPE: DNA
<213> ORGANISM: Rat VNO receptor

<400> SEQUENCE: 10

| | | | | | |
|---|---|---|---|---|---|
| ctgcccattg | gtctcctgtc | cctaatcaac | ttacttatgc | tactgattat | ggcatgtata | 60 |
| gccacagaca | tttttatttc | ttgtagacga | tgggatgaca | tcatatgtaa | atcccttctc | 120 |
| tacctgtaca | gaacttttag | aggtctctct | ctttctacta | cctgcctgtt | gagtgtcctt | 180 |
| caggccatca | tcctcagtcc | cagaagctcc | tgtttagcaa | agtacaaaca | taagcctccc | 240 |
| catcacatct | tctgtgccat | gcttttcctg | agtgtcctct | acatgttcat | tagcagtcac | 300 |
| ctcttactat | ccatcattgc | cacccccaaat | ttgaccacaa | atgactttat | tcatgttagt | 360 |
| cagtcctgct | ctattctacc | catgagttac | ctcatgcaaa | gcatgttttc | tacactgctg | 420 |
| gccatcagga | atgtctttct | tattagcctc | attgtcctct | cgacatggta | catggtggct | 480 |
| ctcttgtgta | ggcacaggaa | acagacccgg | catcttcagg | ataccagcct | tccccgaaaa | 540 |
| gcatctccag | aacaaagggc | cacccgttcc | atcctgatgc | tcaggagctt | atttggtctg | 600 |
| atgtctatct | tcgacagcat | tgcctcct | | | | 628 |

<210> SEQ ID NO 11
<211> LENGTH: 632
<212> TYPE: DNA
<213> ORGANISM: Rat VNO receptor

<400> SEQUENCE: 11

| | | | | | |
|---|---|---|---|---|---|
| tgcccattgg | tctcttgtcc | ctaatccacc | tactgatgct | actgatgggg | gcattcatag | 60 |
| ccatagacat | ttttatttct | tggaggggat | gggatgacat | catatgtaaa | ttccttgtct | 120 |
| acttgtacag | aagttttaga | ggtctctctc | tttgtaccac | ctgcatgttg | agtgtcctgc | 180 |
| aggccatcac | cctcagcccc | agaagctcct | gtttagcaaa | gttcaaacat | aagtctcccc | 240 |
| atcacgtctc | ctgtgccatt | atttcgctga | gcatcctcta | catgttcatt | agcagtcacc | 300 |
| tcttagtatc | catcaatgcc | accccccaatt | tgaccacgaa | caacttttatg | caagttactc | 360 |
| agtcctgcta | cattataccc | ttgagttacc | tcatgcaaag | catgttttct | acacttctgg | 420 |
| ccatcagaga | tatctctctt | attagtctca | tggtcctctc | gacttgttac | atggaggttc | 480 |
| tcttgtgtag | gcacaggaat | cagatccagc | atcttcaagg | gaccaacctt | tccccaaaag | 540 |
| catctccaga | acaaagggcc | acacagacca | tcctgatgct | catgaccttc | tttgtcctaa | 600 |
| tgtccatttt | cgacagcatt | gtctcctgtt | ca | | | 632 |

<210> SEQ ID NO 12
<211> LENGTH: 662
<212> TYPE: DNA
<213> ORGANISM: Rat VNO receptor

<400> SEQUENCE: 12

| | | | | | |
|---|---|---|---|---|---|
| ctacattgca | tccttgtccc | taacacaact | aatgctgctt | ataactatgg | gactcatagc | 60 |
| tgctgacatg | tttatttctc | agggggatatg | ggattctacc | tcatgccagt | cccttatcta | 120 |
| tttgcacagg | ctttcgaggg | gttttaccct | tagtgctgcc | tgtctgctga | atgtcttttg | 180 |
| gatgatcact | ctcagttcta | aaaaatcctg | tttaacaaag | tttaaacata | actctcccca | 240 |
| tcacatctca | ggtgcctttc | ttctcctctg | tgttctctac | atgtgttttta | gcagtcacct | 300 |
| tattttatcg | attattgcta | cccctaactt | gacctcagat | aatttatgt | atgttactaa | 360 |

```
gtcctgttca tttctaccca tgtgttactc cagaacaagc atgttttcca caacaattgc    420
tgtcagggaa gcctttttta tcggtctcat ggccctgtcc agtgggtacc tggtggcttt    480
cctctggaga cacaggaagc aggcccagca tcttcacagc accggccttt cttcaaagtc    540
atctccagag caaagggcca ccgagaccat cctgctgctt atgagtttct tgtggttct    600 ctacattttg gaaaatgttg tcttctactc aaggatgaag ttcaaggatg ggtcaacatt    660
ct                                                                   662
```

<210> SEQ ID NO 13
<211> LENGTH: 653
<212> TYPE: DNA
<213> ORGANISM: Rat VNO receptor

<400> SEQUENCE: 13

```
ttgctttctt atccttaacc caactaatgc tgcttataac tattggactt atagctgcag    60
acatgtttat gtctcggggg agatgggatt ctaccacatg ccagtccctt atctatttgg    120
acaggctttt gagggttttt acccttgtg ctacctgtct gctgaatgtc ctttggacca    180
tcactctcag tcctagaagc tcctgtttaa caacatttaa acataaatct ccccatcaca    240
tctcaggtgc ctttcttttc ttctgtgttc tctatatatc ttttggcagt cacctctttt    300
tatcaacaat tgctaccccc aatttgactt cagataattt tatgtatgtt actaaatcct    360
gttcatttct acccatgagt tactccagaa caagcatgtt ttccacacca atggccatca    420
gggaagccct tcttattggt ctcattggcc tgtccagtgg gtacatggtt gctttcctat    480
ggagacacaa gaatcaggcc cggcatcttc acagcaccag cctttcttca aaagtgtccc    540
cagagcaaag ggccaccagg accatcatga ttctcatgag cttctttgtg gttctctaca    600
ttttggaaaa tgttgtcttc tactctagga tgacattcaa ggatgggtca atg          653
```

<210> SEQ ID NO 14
<211> LENGTH: 628
<212> TYPE: DNA
<213> ORGANISM: Rat VNO receptor

<400> SEQUENCE: 14

```
acctgatcat cagtctcttg gccctcatcc accttgggat gctaacagtc atgggattca    60
gagctgttga tattttgca tctcagaatg tgtggaatga catcaaatgc aaatcccttg    120
cccacttaca cagacttttg aggggcctct ctctttgtgc tacctgtctg ctgagtatct    180
tccaggccat caccccttagc cccagaagct cctgtttagc aaagttcaaa tataaatcca    240
cacagcacag cctgtgttcc cttcttgtgc tctgggcctt ctacatgtcc tgtggtactc    300
actactcctt caccatcgtt gctgactaca acttctcttc acgcagtctc atatttgtca    360
ctgaatcctg cattatttta cccatggatt acatcaccag ggatttattt ttcatattgg    420
ggatatttcg ggatgtgtcc ttcataggtc tcatggccct ctccagcggg tacatggtgg    480
ccctcttgtg cagacacagg aaacaggccc agcatcttca caggaccagc ctttctccaa    540
aagcatcccc agagcaaagg gccaccagga ccatcctgtt gctcatgagc ttctttgtgt    600
tgatgtactg cttggactgc accatatc                                      628
```

<210> SEQ ID NO 15
<211> LENGTH: 636
<212> TYPE: DNA
<213> ORGANISM: Rat VNO receptor -continued

```
<400> SEQUENCE: 15
atctgtgcat tgctttctta tccttaaccc aactaatgct gcttgtaact atgggactca      60
tagctgcaga catgtttatg gctcagggga tatgggatat taccacatgc aggtccctta     120 tctatttttca cagacttttg aggggttttca acctttgtgc tgcctgtcta ctgcatatcc   180
tttggacctt cactctcagt cctagaagct cctgtttaac aaagtttaaa cataaatctc     240
cccatcacat ctcaggtgcc tatctttcct tctgtgttct ctatatgtcc tttagcagtc     300
acctctttgt attggtcatt gctacctcca atttaacctc agatcatttt atgtatgtta     360
ctcagtcctg ctcacttcta cccatgagtt actccagaac aagcacgttt tccttactga     420
tggtcaccag ggaagtcttt cttatcagtc tcatggccct gtccagtggg tacatggtga     480
ctctcctatg gaggcacaag aagcaggccc agcatcttca cagcaccaga ctttcttcaa     540
aagcatcccc acagcaaagg gccaccagga ccatcctgct gcttatgacc ttctttgtgg     600 tttttctacat tttaggcact gttatcttcc actcaa                              636

<210> SEQ ID NO 16
<211> LENGTH: 660
<212> TYPE: DNA
<213> ORGANISM: Homo sapiens

<400> SEQUENCE: 16
ccacgcgtcc gtgatgattc tgtatattta ttcactatga caggtaaatg cctcaggaaa      60
gaaatactta tgtctacagt gagcaagaca gggctagcat cctaggctgt aagtagactg     120
gggttgactc aggagttgaa ccacgaatta aatttgtgat cctggcaaac tgctcaatct     180
ctcagtatct cggtatcctc atacataaga aagggggtgat aatactcatc tcacagagag     240
gtaatgagat aattcacact cagtccttat gccaatgttt tgctcaatat gaatcttcag     300
tgaatattat cagttattaa aatttatttg caagtgtgat gtttgcatta cccacgtttg     360
tcaatgcagt gtttctgtga tattcactgt attaaagaaa ccggagtttc cctttttatg     420
tcttcaattc ctttagttca aactttccat atctttttt attccttgga ttttaatatt      480
tgttttctat tcttttctt tttaaggcag tattatat agtcaaatgg acagacctta        540
catgtgcaat ttaatgagtt gtgacaaatc tgtacactta ggcattcaac atccctatca     600
ggatagaaaa cacttctata ctctcagaaa atttcctctc atgcccctct cagtcaatcc     660

<210> SEQ ID NO 17
<211> LENGTH: 546
<212> TYPE: DNA
<213> ORGANISM: Homo sapiens

<400> SEQUENCE: 17
agcaggctgg taccggtccg gattccggga tatcgtcgac cacgcgtccg ttcggtgact      60
agacggtccg caggggacat cccgtccctg gggcctcccc agtctccctc cccctcgcgc     120
ctgggcagct ctctcccagg gcttcggctc gagcctgcga cctgcacgga cacccccccc     180
tcaggatcta aaatgtccac tgaggcacaa agagttgatg acagtccaag cactagtgga     240
ggaagttccg atggagatca acgtgaaagt gttcagcaag aaccagaaag agaacaagtt     300
cagcccaaga aaaaggaggg aaaaatatcc agcaaaaccg ctgctaaatt gtcaactagt     360
gctaaaagaa ttcagaagga acttgcagaa atcacattgg accctcctcc caactgtagt     420
gctggaccca aaggagacaa catttatgaa atggaggtca actatattgg gacccccagg     480
```

| | |
|---|---|
| atctgtctat taaggagggg tgtttctttc ttgacattac cttttcccag actattcctt | 540 |
| ttaaac | 546 |

<210> SEQ ID NO 18
<211> LENGTH: 2036
<212> TYPE: DNA
<213> ORGANISM: Homo sapiens

<400> SEQUENCE: 18

| | |
|---|---|
| tcgaccccgc gtccgcggac gcgtgggcaa ccatcaaatt gaattaaaaa aaaaaaaaag | 60 |
| aggagcagaa gtttcattgt aagcctttat agcatttgac taatggctat atgcagttct | 120 |
| ctcagtctct tctgcctttg ctggaaatgt atagagtgtt tcttcatcct taggttgaga | 180 |
| gagcataaat atattgaatg gatttgattt cctacaaaac aatattctgg cattttgatt | 240 |
| aattgacgag gaccettcct ttgcaatgta cccaactttt ccttccaaac attagaatgt | 300 |
| ggatcaccta catttgaaga ggtagagctg ataaatctt tgctgatgaa ctaaaaggc | 360 |
| tttcacttca gtgtctggtg aagcaattaa tgctggaaga gtagcttggg gtattaccag | 420 |
| gatgcagcat atggcggtgg tttgctaaag tgatttccat ttggctaacc acttgatggc | 480 |
| aagccagagg cagtatctgg agagaaggta gagttgggaa atgggtcttg agtacatctt | 540 |
| gtcctcaagg cacagggtga tcacagtggt gccttctaag aatgtcagtt agcaacccct | 600 |
| tctcctgcca ccagtgagac agggccattg ttcttcatct ggaagaagcc tctttccttg | 660 |
| ctgaaaggat taggctttga catcaaattc tggctttgac atcattttta agacatcctc | 720 |
| tgaatctaac cctagttttc tgaacaggca aagcctctcg cttaaattca aaattctcca | 780 |
| ggccaaagat gatgtcatgt agttttgaaa ggctccagtt cctggagtac taccaggaaa | 840 |
| agaaagtcat cttccttgaa ttcagtccac cctcaaggtg tcctgagaaa gaagctgttt | 900 |
| ctcagaacag cccaggcaac attgctttca ggcaaactct tctgttgact tcgtatttcc | 960 |
| tacacattct taagccactg aaagagttta agtctgaaag atttctgata cctatttcct | 1020 |
| caccaggctg caaaaatacc agaattattt cattcctgca gcctcaaaga tagagaaatc | 1080 |
| aaggctccaa gagcatgtct tgagctaaaa tagtgatttt ccactttttt taagtgacag | 1140 |
| gatattttca tccaataaaa ctgtggaagg acagattat ttttccactc accagaccag | 1200 |
| tcttcttgac cggtgggcag tgtggagagt tactttcagg ctaccttaa aacgctacct | 1260 |
| gggttctaaa gacaatttat tttttttgtt ggttttttgt ttgttttgt tttgttttgt | 1320 |
| ttgaggcgga gtccctctct gtgttaccca ggctggagtg cagtggcatg atcttggctc | 1380 |
| actgcatcct ccgcctccca tattccagct actcaggagg ctgaggcagg aagatcactt | 1440 |
| gaggccagga gttggagacc agcctgagta acatagcaag acctcattta ttaaaaaata | 1500 |
| aattaataca tagatgatat gattataatg ataaaatgat tataaacagg cacttaataa | 1560 |
| cagacaaaat atatgaacaa aaattgacag aattgagggg agaaatagac aattctacaa | 1620 |
| tagtagttgg agaattatac ccaatatata caggacactc tccccaacaa gataacacta | 1680 |
| cccaacaaca acaggattgc gtatgggaca ttttccagga tagaccatta gttatgccac | 1740 |
| aagttaattt caatagattt ttttaaaga taaatattaa agtatctttt ctgatcacag | 1800 |
| atgaagttag aaaacaataa ccaaggaaa attggaaaat tcacaaattt gtggaaatca | 1860 |
| aacagcacac tcttaaataa ccagtggacc caagaagaa acacatagg taattattag | 1920 |
| aaaatactta gagacgaatg aaaacacaat gtaacaaaac ttatggcaca tgggggaaaa | 1980 |
| cagggcttaa ggaagaaatt tatggtataa atgcttatat taaaaaaaaa aaaaaa | 2036 |

-continued

<210> SEQ ID NO 19
<211> LENGTH: 1965
<212> TYPE: DNA
<213> ORGANISM: Homo sapiens

<400> SEQUENCE: 19

| | | | | | |
|---|---|---|---|---|---|
| tcgacccacg | cgtccgtgcc | cagaaagcat | ccacccacca | tggaaatggc | actgagtaac | 60 |
| cacgtagata | aaacgacttg | actggttgac | atttgtcagc | tttatcacca | gccacccaga | 120 |
| gctgccatga | taggcccatg | agcatcatgg | ccttggtggc | aaagacagag | gttaccaatg | 180 |
| agcccagcag | catgtgcttc | actccaccaag | gtctgtttca | ctactgctgt | tttggaggga | 240 |
| atgcccagct | tgtcagcaac | agacaccagc | actgagccct | taccatggca | cggttcccca | 300 |
| ggggaccaac | agatgcttta | gcagtgagtt | gactctattg | gctcttcccg | tcttggaggg | 360 |
| gctggaggtt | tgtcctcata | gggatgggca | cctcctctgg | gtatgcgatc | acctctccca | 420 |
| cttgcagagc | ctcagctgtc | caggcagctc | tagaaagctc | atgctggctg | ttgaatggaa | 480 |
| actgggctgt | attgagccgg | ttgaagacca | ggaggccatg | aaggagaca | ctgcaacagc | 540 |
| ccagttaaga | gttgataaga | aatgatggct | gggtgacagt | agagatggtg | aaataatagg | 600 |
| attcaagttt | aaaataacga | aaaggtaaac | aatgtgttat | gataaaagct | tactttcttc | 660 |
| taaggcatct | tagacccacc | tttctacatt | ttaatggaca | atacgttctc | tctgattttc | 720 |
| ctctgatcca | atgaatcctt | tgataaaatt | gcaaacaatg | ttttagggtc | ccgcagacac | 780 |
| aaagaaagca | gggtgagtat | ctagtggcat | tgtgcccaga | aagggtgtta | cttttggcaa | 840 |
| aatgaaccag | agcattttcc | aaagtagtat | ttattctttt | taaaattatg | cacgcaacaa | 900 |
| atgtctggt | gagccgactt | ctctaaccca | tgtactaatg | tgtgggtagg | cttataattt | 960 |
| ggggcactca | ctcaggaaat | tctgaaatta | agggtctttc | agaaagtgtt | gactcatccc | 1020 |
| ctccacactt | tctgaatata | tccatttaac | acactaatta | agtaattcta | aattgcattc | 1080 |
| taaattctgc | aggtgatttt | ctgatgaaat | ggtgcttcgc | taattctggt | gggtgttgtt | 1140 |
| tagaatttgc | ttctgcattg | aaaatagctt | tcattttgct | tttgataaaa | atggaaacta | 1200 |
| ttagaaaagg | tccatccaac | tggatatgac | actgtgactc | catcacagtc | tactagtcta | 1260 |
| tgaggtttgc | attcaaatac | ggcactcatg | catctgtttt | tcgcctttga | agaaagcaag | 1320 |
| tccttggtac | aggagagttt | atgagaaaat | cattgttttt | aaatatctat | gtgcaatgcc | 1380 |
| caagaaacat | acatttaatg | tactagacag | tacacaggat | atactctgta | ccatgtatgt | 1440 |
| atttaatcca | ccatttagta | gtttcctgag | actgatcaat | tttctaccat | caatgcctac | 1500 |
| tgcttgatgt | caaactttaa | ttctaattta | aaactaatga | tttcaaatct | taaacaaaag | 1560 |
| taggtattcc | tcactaggag | gcatttacat | agatctttaa | gtgatgcaca | agaaagagt | 1620 |
| aggttttgt | ttttcttttt | tttttttttt | tttcagattt | ctatgttgga | tgcatgtaga | 1680 |
| aagctttcat | attgaagcag | agttttcagt | gaagttggaa | aaagaagaac | aaaggtgaag | 1740 |
| atatccactt | agcaactctc | atcatttgtg | tgtcaccatg | gcttcagaga | cagggataca | 1800 |
| catttagtat | gaaaggagg | cttggaggtt | agcggagagt | tggtggtggt | atagagtaag | 1860 |
| aagacctttt | caaagtttgc | tttcttgaag | agcactagtt | tccctggcat | ggccaatggg | 1920 |
| gtgtttgctg | gtcagtagct | ataacttaaa | gtgcttaaaa | ccaca | | 1965 |

<210> SEQ ID NO 20
<211> LENGTH: 593
<212> TYPE: DNA
<213> ORGANISM: Homo sapiens

```
<400> SEQUENCE: 20
tcgacccacg cgtccgaggc cccggagtag cagcggggag gccgggagcc cgcgggccgg       60
agccgcccgg ccgaggcgtg ggggctgcgg ggccggccca tccgtggggg cgacttgagc      120
gttgagggcg cgcggggagg cgagccacca tgttcagcca gcagcagcag cagcagctcc      180
agcaacagca gcagcagctc cagcagttac agcagcagca gctccagcag cagcaattgc      240
agcagcagca gttactgcag ctccagcagc tgctccagca gtccccacca caggccccgt      300
tgcccatggc tgtcagccgg gggctccccc cgcagcagcc acagcagccg cttctgaatc      360
tccagggcac caactcagcc tccctcctca acggctccat gctgcagaga gctttgcttt      420
tacagcagtt gcaaggactg gaccagtttg caatgccacc agccacgtat gacactgccg      480
gtctcaccat gcccacagca acactgggta acctccgagg ctatggcatg gcatccccag      540
gcctcgcagc ccccagcctc acaccccac aactggccac tccaaatttg caa             593
```